United States Patent
McEntire et al.

(10) Patent No.: US 9,051,639 B2
(45) Date of Patent: Jun. 9, 2015

(54) COATED IMPLANTS AND RELATED METHODS

(75) Inventors: Bryan McEntire, Sandy, UT (US); Ramaswamy Lakshminarayanan, Salt Lake City, UT (US)

(73) Assignee: Amedica Corporation, Salt Lake City, UT (US)

( * ) Notice: Subject to any disclaimer, the term of this patent is extended or adjusted under 35 U.S.C. 154(b) by 159 days.

(21) Appl. No.: 13/619,319

(22) Filed: Sep. 14, 2012

(65) Prior Publication Data
US 2013/0073050 A1    Mar. 21, 2013

Related U.S. Application Data

(60) Provisional application No. 61/535,179, filed on Sep. 15, 2011.

(51) Int. Cl.
*A61F 2/30* (2006.01)
*C23C 14/06* (2006.01)
(Continued)

(52) U.S. Cl.
CPC ............... *C23C 14/0605* (2013.01); *A61F 2/32* (2013.01); *C23C 14/48* (2013.01); *A61F 2002/30695* (2013.01); *A61F 2002/3098* (2013.01); *A61F 2002/30981* (2013.01); *A61F 2310/00179* (2013.01); *A61F 2310/0058* (2013.01); *A61F 2310/00856* (2013.01); *A61L 27/10* (2013.01);
(Continued)

(58) Field of Classification Search
CPC ............ A61F 2002/30014; A61F 2002/30019; A61F 2002/30026
USPC ............. 623/22.11, 22.17, 22.21, 23.42, 23.6
See application file for complete search history.

(56) References Cited

U.S. PATENT DOCUMENTS 3,707,006 A * 12/1972 Bokros et al. ................. 424/422
4,166,292 A *  9/1979 Bokros ....................... 623/21.18
(Continued)

FOREIGN PATENT DOCUMENTS

WO    2013/030787    3/2013

OTHER PUBLICATIONS

International Search Report for PCT/US12/55583, Nov. 21, 2012, 2 pgs.
Written Opinion for PCT/US12/55583, Nov. 21, 2012, 5 pgs.
M. Kiuru, E. Alakoski, V-M. Tiainen, R. Lappalainen and A. Anttila, "Tantalum as a Buffer Layer in Diamond Like Coated Artificial Hip Joints," Journal of Biomedical Materials Research Part B: Applied Biomaterials, vol. 66B, Issue 1, pp. 425-428, Jul. 15, 2003.
R. K. Roy, K-R. Lee, "Biomedial Applications of Diamond-Like Carbon Coatings: A Review," J Biomed Mater Res B Appl Biomater. Oct. 2007;83(1):72-84.
A. Dorner Reisel, C. Schurer, G. Irmer, and E. Muller, Electrochemical Corrosion Behaviour of Uncoated and DLC Coated Medical Grade Co28CnMo, Surface and Coatings Technology, 177-178, 830-837.
(Continued)

*Primary Examiner* — Thomas J Sweet
*Assistant Examiner* — Seema Mathew
(74) *Attorney, Agent, or Firm* — Phillips Ryther & Winchester; Matthew D. Thayne

(57) ABSTRACT

Methods, apparatus, and systems for improving the performance of articulating prostheses. Some embodiments may comprise a first component comprising a first articulating surface and a second component comprising a second articulating surface configured for articulating with the first articulating surface. One or both of the first and second components may comprise a silicon nitride ceramic material. One or both of the first and second articulating surfaces may comprise a coating that is configured to accomplish at least one of increasing the hardness of the first articulating interface surface, reducing the coefficient of friction between the first and second articulating surfaces, decreasing the effects of wearing between the first and second articulating surfaces, and decreasing the intensity of audible noises produced by the endoprosthesis resulting from articulation between the first and second articulating surfaces during use.

21 Claims, 3 Drawing Sheets

(51) Int. Cl.
*A61F 2/32* (2006.01)
*C23C 14/48* (2006.01)
*A61L 27/10* (2006.01)
*A61L 27/30* (2006.01)

(52) U.S. Cl.
CPC ............ *A61L 27/303* (2013.01); *A61L 27/306* (2013.01); *A61L 2420/02* (2013.01); *A61L 2430/02* (2013.01); *C23C 14/0652* (2013.01)

(56) References Cited

U.S. PATENT DOCUMENTS

| | | | |
|---|---|---|---|
| 4,283,799 A * | 8/1981 | Pratt et al. | 623/23.37 |
| 4,957,509 A | 9/1990 | Tamari et al. | |
| 5,370,694 A | 12/1994 | Davidson | |
| 5,593,719 A | 1/1997 | Dearnaley et al. | |
| 5,725,573 A | 3/1998 | Dearnaley et al. | |
| 6,165,616 A * | 12/2000 | Lemelson et al. | 428/408 |
| 6,171,343 B1 | 1/2001 | Dearnaley et al. | |
| 6,517,583 B1 * | 2/2003 | Pope et al. | 623/23.6 |
| 6,534,197 B2 | 3/2003 | Noda et al. | |
| 6,626,949 B1 | 9/2003 | Townley | |
| 6,761,736 B1 | 7/2004 | Woo et al. | |
| 6,793,681 B1 * | 9/2004 | Pope et al. | 623/22.15 |
| 6,881,229 B2 | 4/2005 | Khandkar et al. | |
| 6,994,727 B2 | 2/2006 | Khandkar et al. | |
| 7,077,867 B1 | 7/2006 | Pope et al. | |
| 7,252,684 B2 | 8/2007 | Dearnaley | |
| 7,666,229 B2 | 2/2010 | Khandkar | |
| 7,695,521 B2 | 4/2010 | Ely et al. | |
| 7,704,546 B2 | 4/2010 | Dearnaley | |
| 7,758,646 B2 | 7/2010 | Khandkar et al. | |
| 7,771,481 B2 | 8/2010 | Khandkar et al. | |
| 7,776,085 B2 | 8/2010 | Bernero et al. | |
| 7,780,738 B2 | 8/2010 | Khandkar et al. | |
| 8,066,770 B2 * | 11/2011 | Rivard et al. | 623/16.11 |
| 8,273,130 B2 * | 9/2012 | Gradl | 623/18.12 |
| 8,616,772 B1 | 12/2013 | Kellar et al. | 384/129 |
| 2002/0143402 A1 * | 10/2002 | Steinberg | 623/22.16 |
| 2003/0153984 A1 * | 8/2003 | Khandkar et al. | 623/23.56 |
| 2004/0088052 A1 * | 5/2004 | Dearnaley | 623/16.11 |
| 2005/0154468 A1 * | 7/2005 | Rivin | 623/17.16 |
| 2005/0246025 A1 * | 11/2005 | Kyle | 623/18.11 |
| 2005/0273176 A1 * | 12/2005 | Ely et al. | 623/22.32 |
| 2006/0052875 A1 * | 3/2006 | Bernero et al. | 623/20.33 |
| 2007/0032024 A1 * | 2/2007 | Peidous et al. | 438/299 |
| 2007/0032877 A1 * | 2/2007 | Whiteside | 623/22.15 |
| 2007/0173948 A1 * | 7/2007 | Meridew et al. | 623/22.24 |
| 2007/0233246 A1 * | 10/2007 | Trieu et al. | 623/17.11 |
| 2007/0276492 A1 * | 11/2007 | Andrews et al. | 623/17.11 |
| 2008/0065210 A1 * | 3/2008 | McKay | 623/14.12 |
| 2008/0255674 A1 * | 10/2008 | Rahaman et al. | 623/23.11 |
| 2008/0255675 A1 | 10/2008 | Sidebotham | |
| 2008/0262623 A1 * | 10/2008 | Bagga et al. | 623/17.16 |
| 2009/0005868 A1 * | 1/2009 | Gundlapalli et al. | 623/11.11 |
| 2009/0075114 A1 | 3/2009 | Hovsepian et al. | |
| 2009/0093887 A1 * | 4/2009 | Walter et al. | 623/22.11 |
| 2009/0169845 A1 * | 7/2009 | Leu et al. | 428/216 |
| 2009/0187255 A1 * | 7/2009 | Jani et al. | 623/23.53 |
| 2010/0047434 A1 | 2/2010 | Kumar | |
| 2010/0268337 A1 * | 10/2010 | Gordon et al. | 623/16.11 |
| 2011/0071635 A1 * | 3/2011 | Zhang et al. | 623/17.11 |
| 2011/0130844 A1 * | 6/2011 | Ratron et al. | 623/23.42 |
| 2011/0166671 A1 * | 7/2011 | Kellar et al. | 623/23.53 |
| 2012/0213911 A1 * | 8/2012 | Bucciotti et al. | 427/2.26 |
| 2013/0231750 A1 * | 9/2013 | Taylor | 623/22.21 |
| 2013/0236854 A1 * | 9/2013 | McEntire et al. | 433/173 |
| 2013/0268084 A1 * | 10/2013 | McMinn | 623/22.32 |
| 2014/0005796 A1 * | 1/2014 | Popoola et al. | 623/23.51 |
| 2014/0088721 A1 * | 3/2014 | Boyden et al. | 623/19.11 |
| 2014/0277559 A1 * | 9/2014 | Picha et al. | 623/23.5 |
| 2015/0025647 A1 * | 1/2015 | Zhang | 623/22.18 |

OTHER PUBLICATIONS

V. Saikko, T. Ahiroos, 0 . Calonius, and J. Keranen, Wear Simulation of Total Hip Prostheses with Polyethylene Against Coer, Alumina and Diamond-Like Carbon, Biomaterials, 22, (2001 ), 1507-1514.
S-J. Huang, W-S. Ju, and S-R. Lyu, "A Wear Study of Diamond-Like Carbon Film for Total Hip Arthroplasty Applications," J. of Med and Biolog. Eng., 26, [4], 169-175.
J. M. R Lellis, W. E. Sosa G., and M. C. Ramos, "Evaluation del desgaste de protesis ceramicas de cadera recubiertas con DLC par triboadhesion parte II—pruebas de deposito y desgaste," Revista Mexicana de Ingenieria Biomedica, vol. XXVII, No. 1, Junia 2005, pp. 31-37.
R. Lappalainen, M. Selenius, A. Anttila, Y. T. Konttinen, S. S. Santavirta, "Reduction of Wear in Total Hip Replacement Prostheses by Amorphous Diamond Coatings," Journal of Biomedical Materials Research Part B: Applied Biomaterials, vol. 66B, Issue 1, pp. 410-413, Jul. 15, 2003
M. E. Roy, L.A. Whiteside and B. J. Katerberg, "Diamond-Like Carbon Coatings Enhance Scratch Resistance of Bearing Surfaces for Use in Joint Arthroplasty: Hard Substrates Outperform Soft," Journal of Biomedical Materials Research Part B: Applied Biomaterials, vol. 89B, Issue 2, pp. 527-535, May 2009.
C. Hinuber, C. Kleemann, R. J. Friederichs, L. Haubold, H. J. Scheibe, T. Schuelke, C. Boehlert, and M. J. Baumann, "Biocompatibility and Mechanical Properties of Diamond-Like Coatings on Cobalt-ChromiumMolybdenum Steel and Titanium—Aluminum—Vanadium Biomedical Alloys," J Biomed Mater Res A. Nov. 2010;95(2):388-400.
M. Allen, B. Myer and N. Rushton, "In Vitro and in Vivo Investigations into the Biocompatibility of DiamondLike Carbon (DLC) Coatings for Orthopedic Applications," J Biomed Mater Res. May 1, 2001 ;58(3):319-28.
E. Alakoski, V-M. Tiainen, A. Soininen, and Y. T. Konttinen, "Load-Bearing Biomedical Applications of Diamond-Like Carbon Coatings—Current Status," The Open Orthopedic Journal, 2008, 2, 43-50.
J. Fisher, L Hu, S. Williams, J. L. Tipper, T. Stewart, P. Hatto, M. H. Stone, G. Isaac, C. Hardaker, and E. Ingham, "Surface Engineered Metal on Metal Bearings for Hip Prostheses with Reduced Wear, Wear Debris and Ion Release," 4Efh Annual Meeting of the Orthopaedic Research Society, Paper No. 0102.
G. Dearnaley, "Diamond-Like Carbon: A Potential means of Reducing Wear in Total Joint Replacements," Clinical Materials, 12, (1993), 237-244.
A. Affatato, M. Frigo, and A. Toni, "An In Vitro Investigation of Diamond-Like Carbon as a Femoral Head Coating," J Biomed Mater Res. 2000;53(3):221-6.
C. Liu, Q. Bi, and A. Matthews, "Tribological and Electrochemical Performance of PVD TiN Coatings on the Femoral Head of Ti-6Al-4V Artificial Hip Joints," Surface and Coatings Technology, 163-164 (2003), 597-604.
A.-S. Lair, F. Garrelie, C. Donnet, M. Belin, B. Forest, F. Rogemond and P. Laporte, "Deposition of Tetrahedral Diamond-Like Carbon Thin Films by Femtosecond Laser Ablation for Application of Hip Joints," Thin Solid Films, 453-454, (2004), 531-536.
R. Lappalainen, A. Anttila, and H. Heinonen, "Diamond Coated Total Hip Replacements," Clinical Orthopaedics and Related Research, No. 352, pp. 118-127, (1998).
V-M. Tiainen, "Amorphous Carbon as a Bio-Mechanical Coating—Mechanical Properties and Biological Applications," Diamond and Related Materials, 10, (2000), 153-160.
F. Platon, P. Fournier, and S. Rouxel, "Tribological Behavior of DLC Coatings Compared to Different Materials Used in Hip Joint Prostheses," Wear, 250, (2001 ), 227-236.
E. Salgueiredo, M. Vila, M. A. Silva, M. A. Lopes, J. D. Santos, F. M. Costa, R. F. Silva, P. S. Gomes, and M. H. Fernades, "Biocompatibility Evaluation of DLC-Coated Si3N4 Substrates for Biomedical Applications," Diamond and Related Materials, 17, (2008), 878-881.
J. C. Keurentjes, R. M. Kuipers, D. J. Wever and B. W. Schreurs, High Incidence of Squeaking in THAs with Alumina Ceramic-On-Ceramic Bearings, Clin. Orthop. Relat. Res., (2008) 466:1438-1443.
J. J. Currier, D. E. Anderson and D. W. Van Citters, "A Proposed Mechanism for Squeaking of Ceramic-On-Ceramic Hips," Wear, 269, (2010), 782-789.
L. Mattei, F. Di Puccio, B. Piccigallo and E. Ciulli, "Lubrication and Wear Modelling of Artificial Hip Joints: A Review," Tribology Int., 44, (2011 ), 532-549.

\* cited by examiner

COATED IMPLANTS AND RELATED METHODS

RELATED APPLICATIONS

The present application claims the benefit under 35 U.S.C. §119(e) of U.S. Provisional Patent Application No. 61/535,179 filed Sep. 15, 2011 and titled "COATED IMPLANTS AND RELATED METHODS," which application is incorporated herein by reference in its entirety.

TECHNICAL FIELD

The present disclosure relates generally to implantable prostheses and, more specifically, but not exclusively, to implantable articulating bone prostheses formed from materials having coated articulating interface surfaces.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
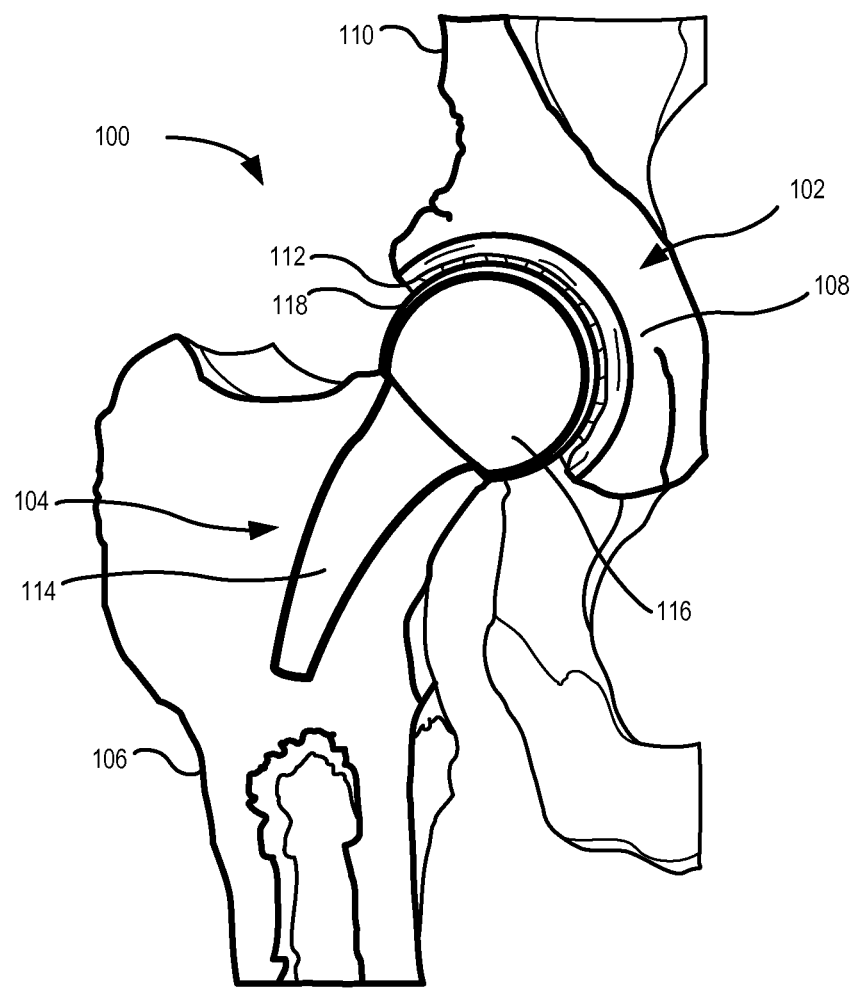
FIG. 1 illustrates a cross sectional view of an exemplary hip prosthesis in an installed position affixed to a patient's femur and acetabulum consistent with embodiments of the present disclosure.

Embodiments may be best understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail.

Implantable articulating bone prostheses and/or implants may conventionally be designed to have metal-on-polyethylene or ceramic-on-polyethylene articulating interface surfaces. For example, a hip joint prosthesis may comprise an acetabular cup seated and/or affixed within a patient's natural acetabulum having an interior interface surface formed of a polyethylene material, and a femoral component formed from metal or ceramic seated and/or affixed within a resected upper end of a patient's femur bone having a ball-shaped femoral head configured to seat within the acetabular cup. The polyethylene material of the polyethylene interior interface surface may be designed to accommodate smooth articulation between the acetabular cup and the femoral component. Premature prosthesis failure can occur, however, due to the generation and accumulation of polymer-based debris associated with the polyethylene interface surface wearing over time.

Articulating bone prostheses and/or implants that include ceramic-on-ceramic articulating interface surfaces may reduce some of the issues associated with polyethylene interface surfaces. While offering certain advantages, ceramic-on-ceramic prostheses may exhibit undesirable audible noises (e.g., "squeaking") when articulated due to a relatively higher coefficient of friction at the articulating interface surfaces. Moreover, due to the nature of certain ceramic materials, ceramic-on-ceramic prostheses may also exhibit undesirable wear on the articulating interface surfaces with extended use.

Consistent with embodiments disclosed herein, an implantable articulating prosthesis (e.g., a bone prosthesis) may be formed from biocompatible ceramics having one or more surfaces, such as one or more articulating interface surfaces, coated with a hard and/or abrasion resistant biocompatible material. The coating material and/or methodology may be selected and/or configured to reduce the intensity of audible noises during articulation of the prosthesis and/or reduce undesirable wear. In addition, or alternatively, the coating material and/or methodology may be configured to reduce the coefficient of friction at the articulating interface surfaces of the prosthesis, thereby improving its overall operation during use. In alternative embodiments, one of the coated articulating surfaces may be made up of a metallic material, and the other coated articulating surface may be made up of a ceramic material.

In some embodiments or implementations, it may also be useful to formulate, engineer, and/or apply coatings such that they have similar properties to that of the substrate. For example, in some such embodiments or implementations, it may be preferable to formulate, engineer, and/or apply one or more coatings that have a modulus of elasticity and/or hardness that is at least close to that of the corresponding substrate.

FIG. 1 illustrates a cross sectional view of an exemplary hip joint prosthesis 100 comprising an acetabular cup 102 and a femoral component 104 both having respective coated articulating interface surfaces. The illustrated hip joint prosthesis 100 is in an installed position affixed to a patient's femur 106 and an acetabulum socket of the patient's pelvis 110, and is configured to repair or replace a natural anatomical ball-and-socket human hip joint. While embodiments are discussed herein in the context of an exemplary hip joint prosthesis 100, the disclosed embodiments may also be implemented in any type of implantable articulating prostheses (e.g., a knee, finger, ankle, or shoulder prosthesis) having any number of articulating components. It is also contemplated that the coatings disclosed herein may be useful in certain non-articulating prostheses. Various embodiments of the invention disclosed herein may also have value for industrial components where low friction bearing surfaces are needed in the presence of only water lubrication, or no lubrication.

The hip joint prosthesis 100 may include an acetabular cup 102 seated and/or affixed within the acetabulum of a patient's pelvis 110. The acetabular cup 102 may be configured to interface with a femoral component 104 including a ball-shaped femoral head 116 configured to seat within the acetabular cup 102, thereby allowing the femoral component 104 to articulate in one or more directions relative to the acetabular cup 102. The femoral component 104 may further include an elongated stem 114 configured to seat and/or be affixed to an upper end of a patient's femur 106. In certain embodiments, the ball-shaped femoral head 116 and the elongated stem 114 may be integral components. In other embodiments, the ball-shaped femoral head 116 and the elongated stem 114 may be selectively detachable components utilizing, for example, a threaded mechanism or locking mechanism for selective detachment.

In certain embodiments, the acetabular cup 102 and/or femoral component 104 may be formed in part of a relatively hard and high strength biocompatible ceramic material which may exhibit ultra-low wear as a consequence of component articulation over an extended service life or duty cycle. In some embodiments, the acetabular cup 102 and the femoral component 104 may be formed of the same ceramic material. The acetabular cup 102 and the femoral component 104 may alternatively be formed of different ceramic materials. As another alternative, one of the acetabular cup and the femoral component may be formed of a metal, and the other of the acetabular cup and the femoral component may be formed of a ceramic material.

In some embodiments, the acetabular cup 102 and/or the femoral component 104 may include relatively porous ceramic bone ingrowth surfaces for secure affixation to a patient's pelvis 110 and/or femur 106. For example, in certain embodiments, the acetabular cup 102 may include a portion 108 having a porous ceramic bone ingrowth configured to be securely affixed to an acetabulum of a patient's femur. In some embodiments, the acetabular cup 102 and/or the femoral component 104 may include first and second regions of differing porosities to respectively mimic natural cortical and cancellous bone structure. In certain embodiments, the higher porosity region may be designed to allow for improved bone ingrowth allowing for more secure and stable affixation of the acetabular cup 102 and femoral component 104 to a patient's pelvis 110 and femur 106 respectively.

In embodiments comprising a ceramic on ceramic, the ceramic material or materials used to form the acetabular cup 102 and the femoral component 104 may comprise one or more high flexural strength and high fracture toughness ceramic materials. In certain embodiments, the ceramic material may comprise a doped silicon nitride ($Si_3N_4$) having relatively high hardness, tensile strength, elastic modulus, lubricity, and fracture toughness properties. Examples of suitable silicon nitride materials are described, for example, in U.S. Pat. No. 6,881,229, which is hereby incorporated by reference in its entirety. Other suitable ceramic materials may include zirconia, alumina, combinations of alumina and zirconia, zirconia toughened alumina (ZTA), and/or other alumina-matrix composites. In certain embodiments, the flexural strength of the ceramic materials may range from approximately 400 Mega-Pascal (MPa) (e.g., for alumina) to approximately 1300 MPa (e.g., for zirconia).

Silicon nitride ceramics in particular have tremendous flexural strength and fracture toughness. In some embodiments, such ceramics have been found to have a flexural strength greater than about 700 MPa. Indeed, in some embodiments, the flexural strength of such ceramics have been measured at greater than about 800 MPa, greater than about 900 MPa, or about 1,000 MPa. The fracture toughness of silicon nitride ceramics in some embodiments exceeds about 7 Mega-Pascal root meter ($Mpa \cdot m^{1/2}$). Indeed, the fracture toughness of such materials in some embodiments is about 7-10 $MPa \cdot m^{1/2}$.

In some embodiments, dopants such as alumina ($Al_2O_3$), yttria ($Y_2O_3$), magnesium oxide, and strontium oxide, can be processed to form a doped composition of silicon nitride. In embodiments comprising a doped silicon nitride or another similar ceramic material, the biocompatible ceramic may have a flexural strength greater than about 900 MPa, and a toughness greater than about 9 $MPa \cdot m^{1/2}$. Flexural strength can be measured on standard 3-point bend specimens per American Society for Testing of Metals (ASTM) protocol method C-1161, and fracture toughness can be measured using single edge notched beam specimens per ASTM protocol method E399. In some embodiments, powders of silicon nitride may be used to form the ceramic implants, either alone or in combination with one or more of the dopants referenced above.

Other examples of suitable silicon nitride materials are described in U.S. Pat. No. 7,666,229 titled "Ceramic-Ceramic Articulation Surface Implants," which is hereby incorporated by reference. Still other examples of suitable silicon nitride materials are described in U.S. Pat. No. 7,695,521 titled "Hip Prosthesis with Monoblock Ceramic Acetabular Cup," which is also hereby incorporated by reference.

In embodiments comprising a metal on ceramic, suitable metals may include various stainless steels, alloys containing cobalt and chromium, titanium, or titanium alloys.

Certain ceramic prostheses may, however, exhibit undesirable audible noises (e.g., "squeaking") when articulated due to a relatively higher coefficient of friction at the articulating interface surfaces. To reduce some of the above-described effects relating to undesirable audible noises (e.g., "squeaking") and/or wear on articulating interface surfaces with extended use, the articulating interface surfaces of the acetabular cup 102 and/or the femoral component 104 may be coated with a hard and/or abrasion resistant biocompatible material. For example, as illustrated, the acetabular cup 102 may include a coating 112 on its interior articulating interface surface. Similarly, the ball-shaped femoral head 116 of the femoral component 104 may include a coating 118 on its exterior articulating interface surface. In some embodiments, both the acetabular cup 102 and the femoral component 104 may include coated articulating interface surfaces. In other embodiments, however, only one of the prosthesis components 102, 104 may include one or more coated articulating interface surfaces.

The coated surfaces 112, 118 may comprise a material selected to reduce the intensity of audible noises during articulation of the prosthesis and/or undesirable wear. In certain embodiments, this may be achieved by selecting a coating material configured to reduce the coefficient of friction at the articulating interface surfaces of the prosthesis 102, 104. In certain embodiments, the coated surfaces 112, 118 may comprise diamond-like carbon ("DLC"), silicon carbide (SiC), titanium nitride (TiN), titanium diboride (TiB2), titanium carbonitride (TiCN), titanium aluminum nitride (TiAlN), chromium nitride (CrN), chromium carbonitride (CrCN), titanium silicon carbonitride (TiSiCN), and/or any other hard, abrasion-resistant, and lubricious material suitable for coating the articulating interface surfaces of the prosthesis components 102, 104. In some embodiments, the coated surfaces 112, 118 may be applied to the articulating interface surfaces of the prosthesis components 102, 104 using any number of suitable methods including, for example, physical vapor deposition ("PVD") or chemical vapor deposition ("CVD") processes. In some embodiments, the coated surfaces 112, 118 may comprise the same coating material. In other embodiments, however, the coated surfaces 112, 118 may comprise different coating materials configured to provide desirable interaction, such as desirable articulation characteristics.

Applying the coated surfaces 112, 118 directly to the ceramic articulating interface surfaces of the prosthesis components 102, 104 may ensure good adhesion of the coated surfaces 112, 118 to the ceramic substrate surfaces. In certain embodiments, this adhesion may be due to covalent bonding between the coated surfaces 112, 118 and the ceramic articulating interface surfaces of the prosthesis components 102, 104. For example, a covalent bond may form between silicon atoms on the surface of an interface surface comprised of silicon nitride ceramic material and carbon atoms in a coating material comprising DLC.

In certain embodiments, applying coated surfaces 112, 118 to the ceramic articulating interface surfaces of the prosthesis components 102, 104 may increase the surface hardness of the articulating interface surfaces. For example, a DLC coating applied using a PVD process may result in a surface hardness ranging from approximately 20 GPa to 40 GPa. A SiC coating applied using a CVD process may result in a surface hardness of approximately 27 GPa. Increasing the surface hardness of the articulating interface surfaces of the prosthesis components 102, 104 by applying the coated surfaces 112, 118 may reduce undesirable wearing of the articulating interface surfaces.

In some embodiments or implementations, it may also be useful to formulate, engineer, and/or apply coatings such that they have similar properties (e.g., a modulus of elasticity and/or hardness value) to that of the substrate. To illustrate, it has been discovered that applying a coating to a substrate, wherein the coating has a much higher modulus of elasticity (e.g., three to five times as high) may, for certain applications and in certain circumstances, lead to an undesirable "candy coating" effect whereby a flexible substrate may have difficulty supporting a relatively inflexible coating. Such an effect may, in certain conditions and circumstances, lead to undesirable chipping, flaking, or other undesirable wear characteristics.

Selecting, engineering, and/or applying such coatings so that certain properties of the coating, such as the modulus of elasticity, more closely match that of their respective substrate may reduce or eliminate these undesirable characteristics. For example, in embodiments in which a DLC coating is applied to a silicon nitride substrate, it may be desirable to formulate, engineer, and/or apply a DLC coating in such a manner that one or more moduli of elasticity and/or hardness values are very similar to that of the silicon nitride. It has been discovered that, in certain implementations, use of a PVD process to apply a DLC coating to a silicon nitride substrate may result in more similar properties than would typically be obtainable using a CVD process. However, in other implementations, the modulus of elasticity and/or other physical characteristics of a DLC coating may be modified to match that of the substrate by providing suitable additives in addition to, or as an alternative to, using a PVD process.

Examples of additives that may be used to modify the modulus of elasticity of the coating include, but are not limited to, silicon, carbon, chromium, titanium, vanadium, manganese, nitrogen, oxygen, aluminum, and tantalum. Also, applying the additive as an interlayer, or multiple interlayers, or a graded interlayer, may be effective in adjusting the modulus of elasticity and/or hardness of a DLC coating.

More particularly, in some embodiments and implementations, the Young's modulus of elasticity of the coating may be selected and/or applied such that it is within about 100 GPa of the Young's modulus of elasticity of the substrate. In some such embodiments, the Young's modulus of elasticity of the coating may be within about 50 GPa of the Young's modulus of elasticity of the substrate.

In some embodiments and implementations, the Young's modulus of elasticity of the coating may be selected and/or applied such that it is within about 10% of the Young's modulus of elasticity of the substrate. In some such embodiments, the Young's modulus of elasticity of the coating may be within about 5% of the Young's modulus of elasticity of the substrate.

To illustrate with more specific examples, the Young's modulus of elasticity of some embodiments of the doped silicon nitride ceramics disclosed herein may be in the range of about 300 GPa to about 320 GPa. In such embodiments, the Young's modulus of elasticity of the coating may be within a range of about 220 to about 400 GPa.

In addition to using a CVD process, it may be useful to apply one or more pre-treatment processes before coatings are applied. For example, in some implementations, an ion implantation process may be employed. In such a process, carbon ions may be implanted into the surface of a substrate to provide a network structure for improved adhesion of the coating. In some implementations, this pre-treatment process may comprise a high-power impulse magnetron sputtering (HiPIMS) process.

As discussed above, the coated surfaces 112, 118 may also reduce the coefficient of friction at the articulating interface surfaces of the prosthesis components 102, 104. In some embodiments, reducing the coefficient of friction at the articulating interface surfaces of the prosthesis components 102, 104 may result in a lower intensity of, and/or fewer, audible noises produced by the prosthesis 100 during use. For example, in certain embodiments, an uncoated ceramic articulating interface surface may have a coefficient of friction ranging from approximately 0.1 to 0.4, whereas a coated articulating interface surface (e.g., coated using DLC) may have a coefficient of friction on the order of about 0.01 to about 0.1. Reducing the coefficient of friction at the articulating interface surfaces of the prosthesis components 102, 104 may also reduce wear on the components 102, 104 and/or extend in-vivo longevity of the prosthesis.

Figure 2:
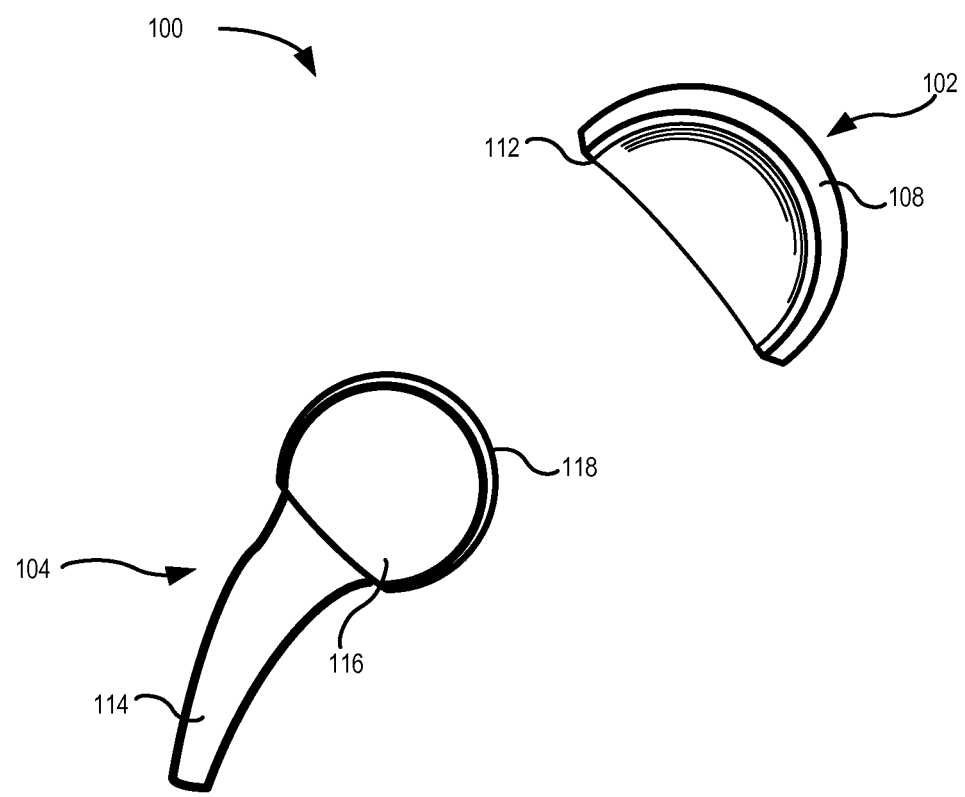
FIG. 2 illustrates an exploded view of an exemplary hip prosthesis consistent with embodiments of the present disclosure.

FIG. 2 illustrates an exploded view of the exemplary hip prosthesis 100 described above in reference to FIG. 1. As illustrated, the exemplary hip prosthesis 100 may comprise an acetabular cup 102 and/or femoral component 104 formed of a relatively hard and high strength biocompatible ceramic material. The femoral component 104 may include a ball-shaped femoral head 116 configured to seat within the acetabular cup 102 and an elongated stem 114 that may be integral with or selectively detachable from the ball-shaped femoral head 116.

The articulating interface surfaces of the acetabular cup 102 and/or the femoral component 104 may include coatings 112, 118 comprising a hard and/or abrasion resistant biocompatible material such as, for example, DLC or SiC. As discussed above, the material of coatings 112, 118 may be selected to increase the hardness of the articulating interface surfaces, reduce the coefficient of friction between the two components 102, 104, decrease the effects of wearing at the articulating interface surfaces, and/or decrease the intensity of audible noises produced by the prosthesis 100 during use. Moreover, the material of coatings 112, 118 may be selected from suitable materials that form covalent bonds with a material used to form one or both of the prosthesis components 102, 104 when deposited on the material of the acetabular cup 102 and/or the femoral component 104.

Figure 3:
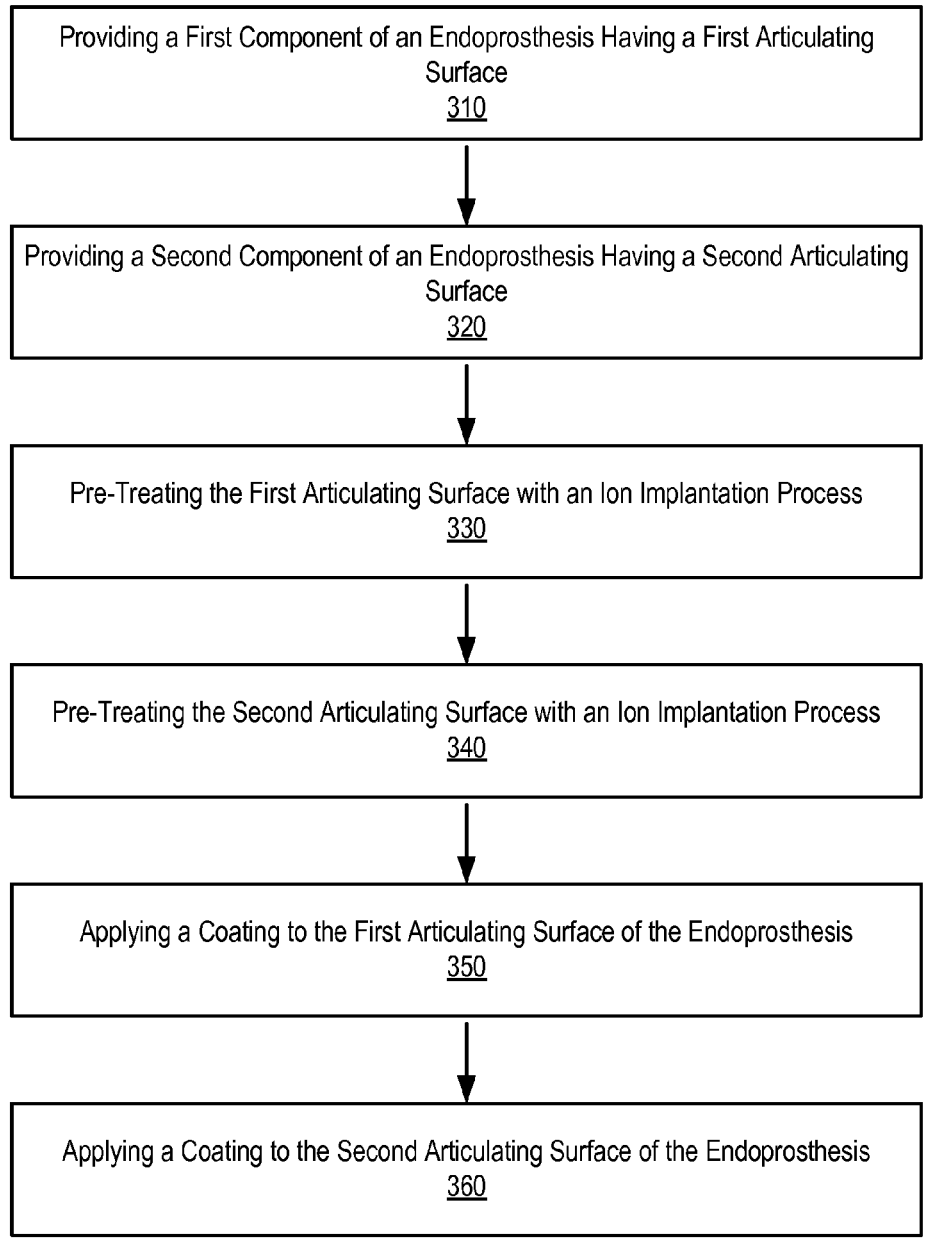
FIG. 3 is a flow chart of one implementation of a method for forming a coating on a ceramic implant.

FIG. 3 is a flow chart showing one implementation of a method for forming a coated ceramic prosthesis. At step 310, a first component of an endoprosthesis is provided. The first component has a first articulating surface. At step 320, a second component of the endoprosthesis is provided. The second component has a second articulating surface that is configured to articulate with the first articulating surface.

At step 330, the first articulating surface is pre-treated with an ion implantation process. As described in greater detail above, the ion implantation process may comprise a process for implanting carbon ions into the first articulating surface.

The ion implantation process may, in some implementations, comprise a high-power impulse magnetron sputtering (HiPIMS) process.

At step 340, the second articulating surface is also pretreated with an ion implantation process. As with step 330, the ion implantation process for the second articulating process may comprise a process for implanting carbon ions into the second articulating surface. In some implementations, step 340 may comprise a high-power impulse magnetron sputtering (HiPIMS) process.

At step 350, a coating may be applied to the first articulating surface of the endoprosthesis. As described in detail above, the coating may comprise a diamond-like carbon ("DLC"), silicon carbide (SiC), titanium nitride (TiN), titanium diboride (TiB2), titanium carbonitride (TiCN), titanium aluminum nitride (TiAlN), chromium nitride (CrN), chromium carbonitride (CrCN), titanium silicon carbonitride (TiSiCN), and/or any other hard, abrasion-resistant, and lubricious material suitable for coating the articulating interface surfaces of prosthesis components. The process for applying the coating in step 350 may comprise, for example, a physical vapor deposition ("PVD") or a chemical vapor deposition ("CVD") process. The coating may be configured to accomplish at least one of increasing the hardness of the first articulating interface surface, reducing the coefficient of friction between the first and second articulating surfaces, decreasing the effects of wearing between the first and second articulating surfaces, and decreasing the intensity of audible noises produced by the endoprosthesis resulting from articulation between the first and second articulating surfaces during use.

The coating may also be selected and/or applied so as to substantially match one or more physical characteristics of the first articulating surface. For example, in some implementations, the coating may be selected and applied such that the Young's modulus of elasticity of the coating is within about 10% of the Young's modulus of elasticity of the first articulating surface. In some such embodiments, the Young's modulus of elasticity of the coating may be within about 5% of the Young's modulus of elasticity of the first articulating surface. As another example, the coating may be selected and applied such that the Young's modulus of elasticity of the coating is within about 100 GPa of the Young's modulus of elasticity of the first articulating surface. In some such embodiments, the coating may be selected and applied such that the Young's modulus of elasticity of the coating is within about 50 GPa of the Young's modulus of elasticity of the first articulating surface.

At step 360, a coating may also be applied to the second articulating surface of the endoprosthesis. As with the coating on the first articulating surface, the coating may comprise a diamond-like carbon ("DLC"), silicon carbide (SiC), titanium nitride (TiN), titanium diboride (TiB2), titanium carbonitride (TiCN), titanium aluminum nitride (TiAlN), chromium nitride (CrN), chromium carbonitride (CrCN), titanium silicon carbonitride (TiSiCN), and/or any other hard, abrasion-resistant, and lubricious material suitable for coating the articulating interface surfaces of prosthesis components. Similarly, the process for applying the coating in step 360 may comprise, for example, a physical vapor deposition ("PVD") or a chemical vapor deposition ("CVD") process. The coating may be configured to accomplish at least one of increasing the hardness of the second articulating interface surface, reducing the coefficient of friction between the first and second articulating surfaces, decreasing the effects of wearing between the first and second articulating surfaces, and decreasing the intensity of audible noises produced by the endoprosthesis resulting from articulation between the first and second articulating surfaces during use.

The coating may also be selected and/or applied so as to substantially match one or more physical characteristics of the second articulating surface. For example, in some implementations, the coating may be selected and applied such that the Young's modulus of elasticity of the coating is within about 10% of the Young's modulus of elasticity of the second articulating surface. In some such embodiments, the Young's modulus of elasticity of the coating may be within about 5% of the Young's modulus of elasticity of the second articulating surface. As another example, the coating may be selected and applied such that the Young's modulus of elasticity of the coating is within about 100 GPa of the Young's modulus of elasticity of the second articulating surface. In some such embodiments, the coating may be selected and applied such that the Young's modulus of elasticity of the coating is within about 50 GPa of the Young's modulus of elasticity of the second articulating surface.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. In addition, it should be understood that other implementations of such methods need not necessarily include each of the recited steps.

Throughout this specification, any reference to "one embodiment/implementation," "an embodiment/implementation," or "the embodiment/implementation" means that a particular feature, structure, or characteristic described in connection with that embodiment/implementation is included in at least one embodiment/implementation. Thus, the quoted phrases, or variations thereof, as recited throughout this specification are not necessarily all referring to the same embodiment/implementation.

Similarly, it should be appreciated that in the above description of embodiments, various features are sometimes grouped together in a single embodiment, implementation, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments and implementations without departing from the underlying principles set forth herein.

The invention claimed is:

1. An articulating endoprosthesis, comprising:
    a first component comprising a first articulating surface, wherein the first component comprises a silicon nitride ceramic material;
    a second component comprising a second articulating surface configured for articulating with the first articulating surface, wherein the second component comprises a silicon nitride ceramic material;
    a first coating positioned on the first articulating surface, wherein the first coating is configured to decrease the intensity of audible noises produced by the endoprosthesis resulting from articulation between the first and second articulating surfaces during use, wherein the first coating has a Young's modulus of elasticity that is within about 10% of the Young's modulus of elasticity of the first articulating surface; and a second coating positioned on the second articulating surface, wherein the second coating is configured to decrease the intensity of audible noises produced by the endoprosthesis resulting from articulation between the first and second articulating surfaces during use, and wherein the second coating has a Young's modulus of elasticity that is within about 10% of the Young's modulus of elasticity of the second articulating surface.

2. The endoprosthesis of claim 1, wherein the first coating comprises a diamond-like carbon material, and wherein the second coating comprises a diamond-like carbon material.

3. The endoprosthesis of claim 1, wherein the endoprosthesis comprises a hip joint prosthesis.

4. The endoprosthesis of claim 1, wherein the first coating has a Young's modulus of elasticity that is within about 5% of the Young's modulus of elasticity of the first articulating surface, and wherein the second coating has a Young's modulus of elasticity that is within about 5% of the Young's modulus of elasticity of the second articulating surface.

5. An articulating endoprosthesis, comprising:
a first component comprising a first articulating surface, wherein the first component comprises a silicon nitride ceramic material;
a second component comprising a second articulating surface configured for articulating with the first articulating surface; and
a coating positioned on the first articulating surface, wherein the coating is configured to accomplish at least one of increasing the hardness of the first articulating interface surface, reducing the coefficient of friction between the first and second articulating surfaces, decreasing the effects of wearing between the first and second articulating surfaces, and decreasing the intensity of audible noises produced by the endoprosthesis resulting from articulation between the first and second articulating surfaces during use, and wherein the coating has a Young's modulus of elasticity that is within about 100 GPa of a Young's modulus of elasticity of the first articulating surface.

6. The endoprosthesis of claim 5, wherein the second component comprises a silicon nitride ceramic material.

7. The endoprosthesis of claim 6, further comprising a second coating positioned on the second articulating surface, wherein the second coating is configured to accomplish at least one of increasing the hardness of the second articulating interface surface, reducing the coefficient of friction between the first and second articulating surfaces, decreasing the effects of wearing between the first and second articulating surfaces, and decreasing the intensity of audible noises produced by the endoprosthesis resulting from articulation between the first and second articulating surfaces during use.

8. The endoprosthesis of claim 5, wherein the second component comprises a metallic material.

9. The endoprosthesis of claim 8, further comprising a second coating positioned on the second articulating surface, wherein the second coating is configured to accomplish at least one of increasing the hardness of the second articulating interface surface, reducing the coefficient of friction between the first and second articulating surfaces, decreasing the effects of wearing between the first and second articulating surfaces, and decreasing the intensity of audible noises produced by the endoprosthesis resulting from articulation between the first and second articulating surfaces during use.

10. The endoprosthesis of claim 5, wherein the coating comprises at least one of diamond-like carbon, silicon carbide, titanium nitride, titanium diboride, titanium carbonitride, titanium aluminum nitride, chromium nitride, chromium carbonitride, and titanium silicon carbonitride.

11. The endoprosthesis of claim 5, wherein the coating comprises diamond-like carbon.

12. The endoprosthesis of claim 5, wherein the endoprosthesis comprises a hip joint prosthesis.

13. The endoprosthesis of claim 5, wherein the first articulating surface has a coefficient of friction between about 0.01 and about 0.1.

14. The endoprosthesis of claim 5, wherein the coating has a Young's modulus of elasticity that is within about 50 GPa of the Young's modulus of elasticity of the first articulating surface.

15. The endoprosthesis of claim 1, wherein the first coating has a Young's modulus of elasticity that is within about 100 GPa of the Young's modulus of elasticity of the first articulating surface, and wherein the second coating has a Young's modulus of elasticity that is within about 100 GPa of the Young's modulus of elasticity of the second articulating surface.

16. The endoprosthesis of claim 15, wherein the first coating has a Young's modulus of elasticity that is within about 50 GPa of the Young's modulus of elasticity of the first articulating surface, and wherein the second coating has a Young's modulus of elasticity that is within about 50 GPa of the Young's modulus of elasticity of the second articulating surface.

17. The endoprosthesis of claim 5, further comprising an interlayer positioned in between the first articulating surface and the coating, wherein the interlayer comprises at least one of silicon, carbon, chromium, titanium, vanadium, manganese, nitrogen, oxygen, aluminum, and tantalum.

18. The endoprosthesis of claim 17, wherein the interlayer comprises a graded interlayer.

19. The endoprosthesis of claim 17, wherein the interlayer comprises carbon.

20. The endoprosthesis of claim 7, wherein the second coating has a Young's modulus of elasticity that is within about 10% of the Young's modulus of elasticity of the second articulating surface.

21. The endoprosthesis of claim 20, wherein the second coating has a Young's modulus of elasticity that is within about 5% of the Young's modulus of elasticity of the second articulating surface.

* * * * *